(12) United States Patent  
Landy et al.

(10) Patent No.: US 7,819,835 B2  
(45) Date of Patent: Oct. 26, 2010

(54) HYPERTHERMIA, SYSTEM, METHOD AND COMPONENTS

(75) Inventors: John Landy, Billerica, MA (US); Michael Gildersleeve, Northborough, MA (US); Yeu Wen Peter Tseng, Acton, MA (US)

(73) Assignee: Belmont Instrument Corporation, Billerica, MA (US)

( * ) Notice: Subject to any disclaimer, the term of this patent is extended or adjusted under 35 U.S.C. 154(b) by 187 days.

(21) Appl. No.: 11/890,577

(22) Filed: Aug. 7, 2007

(65) Prior Publication Data

US 2009/0043256 A1 Feb. 12, 2009

(51) Int. Cl.
- A61M 37/00 (2006.01)
- A61F 7/00 (2006.01)
- A61F 7/12 (2006.01)
- A61F 2/00 (2006.01)
- A61B 18/04 (2006.01)

(52) U.S. Cl. ............... 604/6.13; 604/291; 606/27; 607/21; 607/96; 607/103; 607/104

(58) Field of Classification Search .......... 604/291, 604/6.13, 113, 21, 96; 606/24, 27, 28
See application file for complete search history.

(56) References Cited

U.S. PATENT DOCUMENTS

| 5,476,444 | A * | 12/1995 | Keeling et al. ............ 604/6.13 |
| 2001/0039441 | A1 * | 11/2001 | Ash ............................ 607/106 |
| 2003/0139788 | A1 * | 7/2003 | Eggers et al. .................. 607/96 |
| 2006/0089586 | A1 * | 4/2006 | Kaus et al. .................. 604/4.01 |

* cited by examiner

*Primary Examiner*—Nicholas D Lucchesi
*Assistant Examiner*—Rebecca E Eisenberg
(74) *Attorney, Agent, or Firm*—Morris I. Pollack

(57) ABSTRACT

An IV pole mountable, therapeutic infusate processing device is incorporated into a hypothermia system to receive therapeutic fluid(s), such as normal saline, peritoneal dialysis solution, or other crystalloid solution, to heat such therapeutic fluid(s) a few degrees centigrade above normal body temperature and to direct the resulting heated infusate to and through a selected anatomical portion of a patients body to raise the temperature of that body portion so as to affect any cancerous or other tumors that may be located therein. The processing device is provided with touch screen controls and visual indicators to facilitate its proper use; while the system further includes temperature and pressure sensors to monitor the hyperthermia processing to insure patient safety.

12 Claims, 7 Drawing Sheets

| RATE = 750 ml/min | Tout = 42.5°C |
| VOL = 16.2 L | T1 = 42.3°C |
| P = 125 mmHg | T2 = 42.0°C |
| RATE ▲ | | TARGET ▲ 42.5°C | STOP |
| RATE ▼ | | TARGET ▼ 42.5°C | |

HYPERTHERMIA, SYSTEM, METHOD AND COMPONENTS

BACKGROUND OF THE INVENTION

1. Field of Application

This invention relates to the treatment of diseases by raising body temperature; and more particularly to raising the temperature of a specific anatomical portion or portions of a body.

2. Description of the Prior Art

Hyperthermia as a treatment of tumors has been carefully studied and applied. There appear to have been multiple reports of tumor regression coincident with febrile episodes. Some analysis revealed that body temperatures greater than 41 degree. C. are ordinarily needed to induce tumor necrosis (tumor death). Although, there are multiple methods of inducing hyperthermia by either direct skin contact or radiant heating, many physicians have favored an extracorporeal heat exchange (blood) circuit to raise patient body temperatures. Some patients have been maintained at 41.5 degrees to 42 degrees. C. (rectal temperature) for three to four hours without severe cardiovascular compromise; however, others have suffered elevation of serum transaminases and bilirubin when kept at such temperatures for greater than 10 to 40 minutes. There have also been Instances of neurological damage in association with serum hypophosphatemia, although no significant problems occurred once phosphate levels were maintained. Death may also occur for patients receiving hyperthermia at 41.5 degree. to 42 degree. C. for 1½ to hours, presumably from massive liver tumor necrosis.

U.S. Pat. No. 2,886,771 to Vincent; No. 3,482,575 to Claff; No. 4,061,141 to Hyden, No. 4,191,182 to Popovich; No. 4,321,918 to Clark; No. 4,322,275 to Jain; No. 4,381,004 to Babb; No. 4,479,798 to Parks; No. 4,540,401 to Marten; No. 4,563,170 to Aigner; No. 4,576,143 to Clark and No. 4,692, 188 to Troutner et al.; all relate to methods for the extracorporeal treatment of blood for cancers, viruses and parasites. Tumors are vulnerable to heat and the goal of hyperthermic treatment therapy is to achieve cytotoxic temperatures in the tumor for a sufficient length of time without damaging the surrounding normal tissue. The rate at which blood flows through any given area of tissue determines the amount of heat that may be carried away and therefore is a major determinant of the temperature rise in that tissue. In normal tissue, heat causes vasodilatation. In a tumor, the microvasculature is made up of an overabundance of capillary beds, which are unable to dilate. Blood flow through the area is thus more sluggish and commensurately unable to dissipate heat applied to the area. The inability to respond to heat by dilation, as normal vasculature would, also subjects the tumor to hypoxia, anaerobic metabolism and local acidosis, and these conditions in turn make the tumor tissue more vulnerable to thermal injury.

U.S. Pat. No. 5,354,277 and No. 5,476,444 are directed to methods and apparatus for effecting whole-body hyperthermia: however, the equipment and procedures disclosed appear to suffer from relatively difficult temperature controls for the fluid handling systems; possible risk of contamination; and possible difficulty to optimize the fluid handling system for a particular indication.

Some physicians, on the other hand, favor heating only body cavities, such as the peritoneal, and/or chest, cavity with heated fluids to create hyperthermia of the respective tissue surfaces within the cavity. U.S. Pat. No. 6,579,496 and No. 6,827,898 appear to be directed to not only body hyperthermia through extracorporal blood heating with circulation of the heated blood through a patient; but also to heating a therapeutic fluid for passage through a regional anatomical area of the body. These patents describe systems which kluge together hospital available equipment such as hemodialysis machines with tubular heat exchangers and high flow positive displacement pumps. The resulting equipment appears to be large and cumbersome, for the task and for the relatively tight hospital quarters for the patient. In addition, the heating of therapeutic fluids, that are to pass through the patient's body, and the passing of such fluids through the patient's body, at such elevated temperatures and flow rates, could be damaging to the patient and even more detrimental to the patient then the disease to be treated.

SUMMARY OF THE INVENTION

It is therefore an object of this invention to provide new and novel systems for implementing hyperthermia.

It is another object of this invention to provide new and novel methods for implementing hyperthermia.

It is yet another object of this invention to provide new and novel apparatus for incorporation into hyperthermia implementation systems and methods.

It is yet still another object of this invention to provide new and novel hyperthermia systems to be used in therapeutic procedures in which fluid is held at a few degrees centigrade above normothermic to be pumped into a body cavity and continuously withdrawn and reheated.

It is yet still another object of this invention to provide new and novel hyperthermia systems and methods, to be used in therapeutic procedures, in which the combination of temperature and fluid flow rate for therapeutic fluid(s) used thereby are optimized and may be operation set.

It is yet still another object of this invention to provide new and novel hyperthermia systems and methods, to be used in therapeutic procedures, in which the combination of temperature and fluid flow rate for therapeutic fluid(s) are optimized, by heating the therapeutic fluid to only a few degrees C, above normothermic, and, by circulating, withdrawing and re-circulating such fluid, to and through a body cavity, at a flow rate commensurate with the selected temperature; to provide an efficient hyperthermia system and method which is relatively effective and safe for the patient, and may be operator set.

It is yet still another object of this invention to provide new and novel hyperthermia systems to be used in therapeutic procedures in which therapeutic fluid is held at a few degrees centigrade above normothermic to be pumped into a body cavity at a relatively safe flow rate while being continuously withdrawn and reheated.

It is yet still another object of this invention to provide a new and novel system and method for heating infusion fluids in which such fluids are heated to a predetermined temperature during slack time between infusion demands, and held as so heated in anticipation of future use.

It is yet still another object of this invention to provide new and novel hyperthermia systems to be used in therapeutic procedures in which the infusion fluid is heated to a predetermined temperature during slack time, between infusion demands, and held as so heated in anticipation of future use.

It is yet still another object of this invention to provide new and novel hyperthermia systems to be used in therapeutic procedures in which the infusion fluid is heated to a predetermined temperature during slack time, between infusion demands and without intervention of an operator, and held as so heated in anticipation of future use.

It is yet still another object of this invention to provide new and novel and disposable fluid administration sets which are constructed of materials that can be sterilized and made pyrogen free by conventional methods and so that single use thereof is economically feasible.

It is yet still another object of this invention to provide new and novel disposable fluid administration sets which are constructed of materials that are free of latex and DEHP.

Other objects of this invention will hereinafter become obvious from the following description of the preferred embodiments of this invention.

The instant hyperthermia system and method utilizes therapeutic fluid heated to only a few degrees above normothermic and which is pumped at a reasonable flow rate. The system monitors fluid temperature, line pressure, and air in the fluid path to ensure safe operation and alarms at all unsafe conditions. An override circuit prevents unsafe operation in case of system computer failure. A touch screen displays flow rate, total fluid pumped, output temperature, patient temperature (2 locations specified by the physician), line pressure, alarm and status messages and proper procedures to proceed safely after an alarm situation. Keys appropriate to a particular point in the operation are displayed on the touch screen.

DESCRIPTION OF THE INVENTIVE EMBODIMENTS

Figure 1:
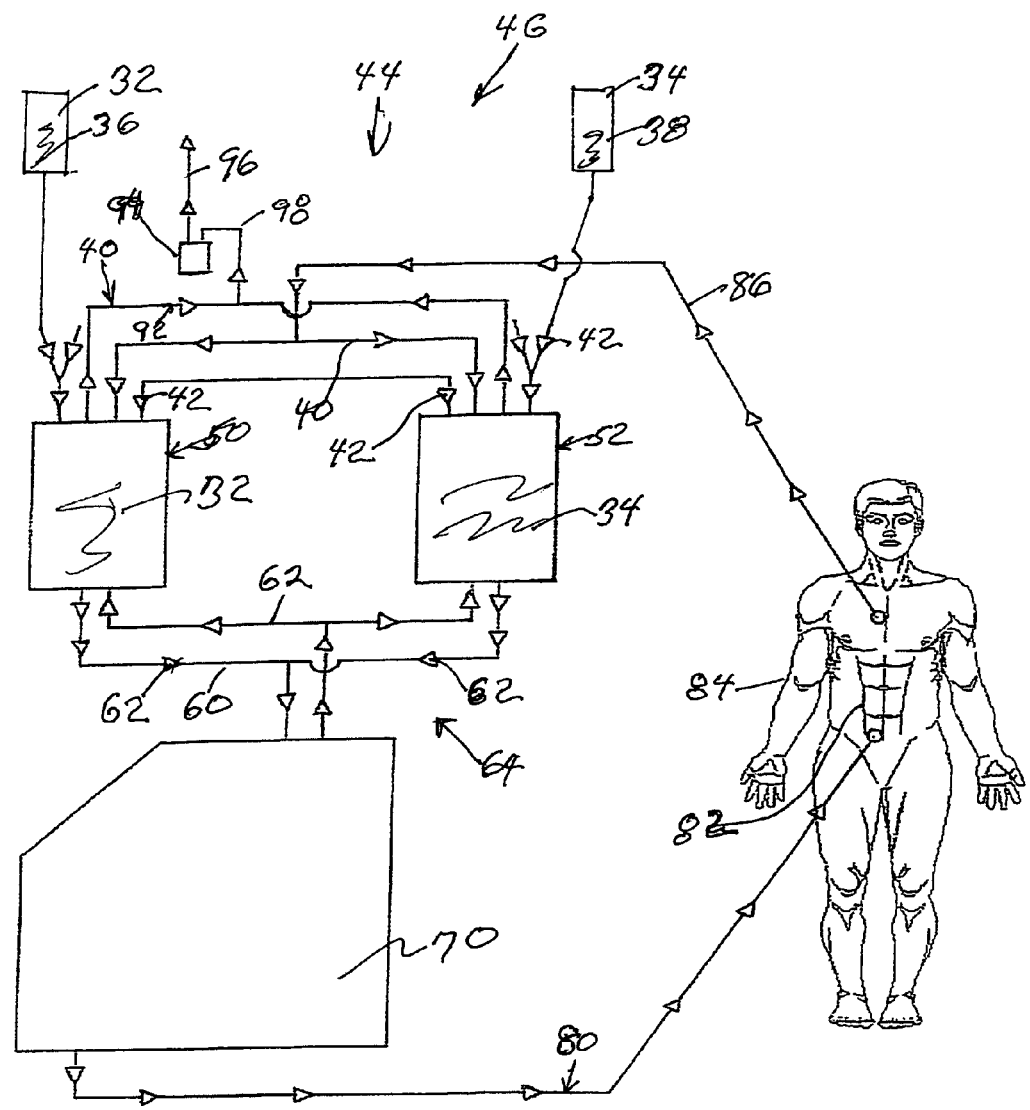
FIG. 1 is a diagram of the hyperthermia system and method, incorporating and embodying the principals of and the instant invention, shown with a representation of a patient's body.
Figure 2:
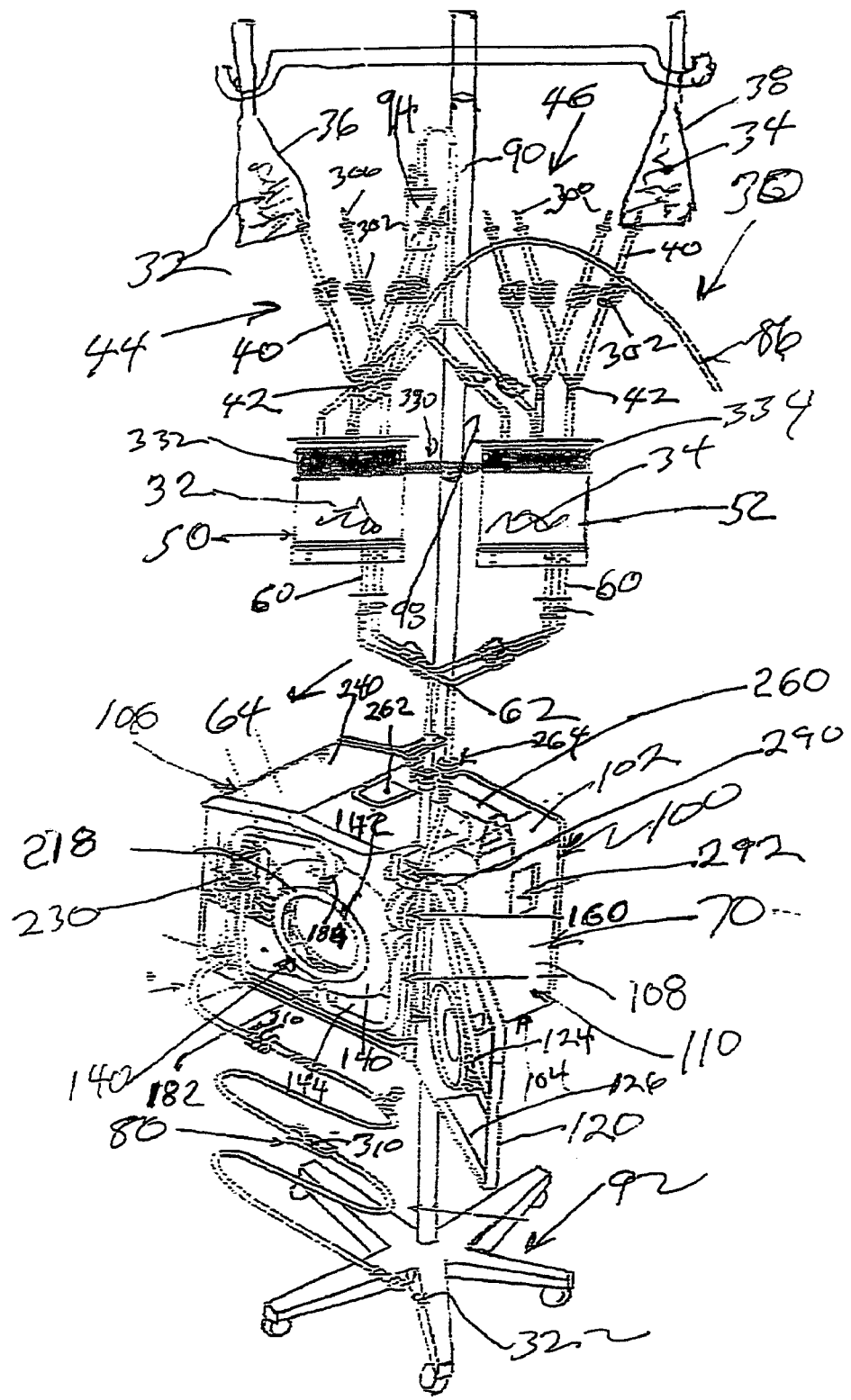
FIG. 2 is a perspective elevation view of a therapeutic fluid processing device incorporating the instant invention and which includes a fluid heater and pump, shown with a disposable IV set, also incorporating the instant invention, positioned for co-action with the mechanisms of the fluid processing device, all as mounted upon an IV pole.

With reference to FIGS. 1 & 2, there is generally shown at 30 a hyperthermia system, incorporating the instant invention. Therapeutic infusion fluid(s) 32, and/or 34, are provided to system 30 from either one or more conventionally available IV type bags 36, 38. Fluid tubular lines 40 and "Y" connectors 42, of section 44 of an infusion fluid disposable set 46, direct infusion fluid 32, 34 to reservoirs 50, 52, of the infusion fluid disposable set 46; for storage and further use as will be described in greater detail hereinafter. Additional tubular fluid lines 60 and "Y" connectors 62, of section 64 of disposable set 46, direct fluid(s) 32, 34 from reservoirs 50, 52 to and through a therapeutic fluid processing device 70. Therapeutic fluid 32, 34 after being processed by device 70 is directed into a patient tubular fluid feed line 80 (FIG. 1) to a respective anatomical portion 82 of a patient's body 84, and then, from that anatomical portion 82, by a patient tubular fluid return line 86 back to and through fluid lines 40 and "Y" connectors 42 to reservoirs 50 and or 52. Fluid feed line 80, and fluid return line 86 together constitute a patient's line 88 (FIGS. 2, 6) that may be provided as two separate lines or as a single patient line 88 of predetermined length to be divided into feed line 80 and return line 86 as it is required and as will be hearing after explained in grater detail.

Figure 4:
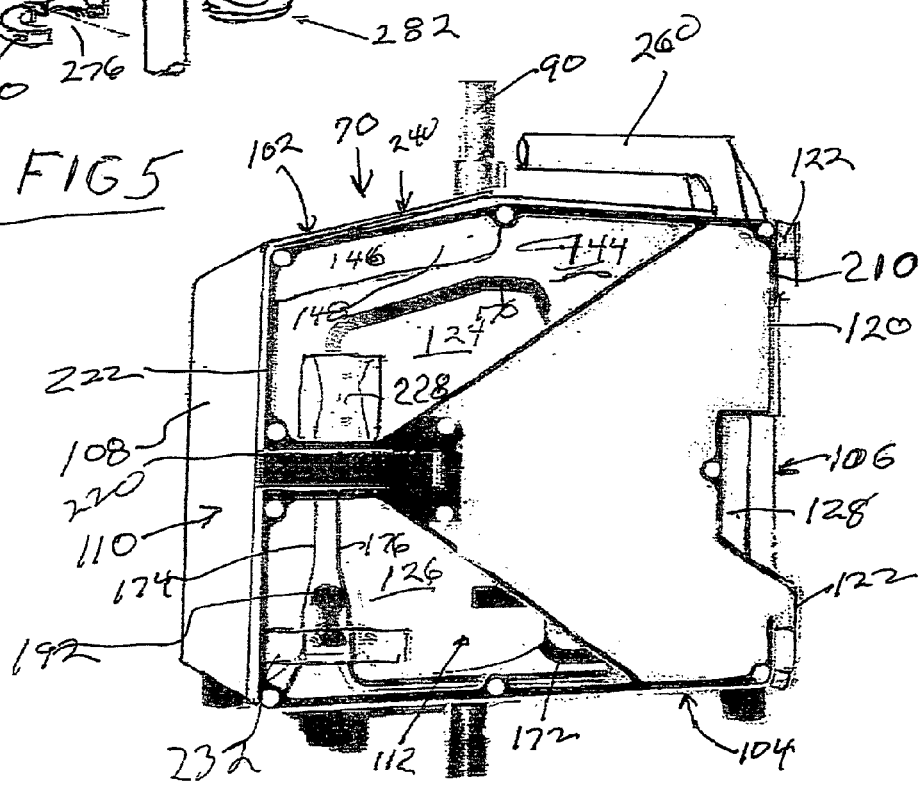
FIG. 4 is a perspective elevation view of the fluid processing device of FIGS. 2 & 3 showing same being mounted to the IV pole with its access door closed.

Therapeutic fluid processing device 70 is of a weight, size and configuration that permit it to be mounted to, and utilized when, carried by a conventional IV pole 90 (FIGS. 2, 4 & 5) whether, or not, such IV pole is provided with a wheel base 92 as shown in FIG. 2. Device 70 may just as easily be utilized when positioned on a substantially horizontal surface such as a table, cabinet or the like as long as it is in proximity to the patient that is to undergo the intended procedure.

A vacuum trap 94 (FIGS. 1, 2 and 6) is connected by a suitable vacuum line 96 (FIG. 1) to the vacuum regulator/wall suction (not shown) of the location (hospital, etc.) where patient 84 is to be treated and by a vacuum line 98 (FIGS. 1, 2 and 6) and "Y" to the top of reservoirs 50, 52.

Figure 3:
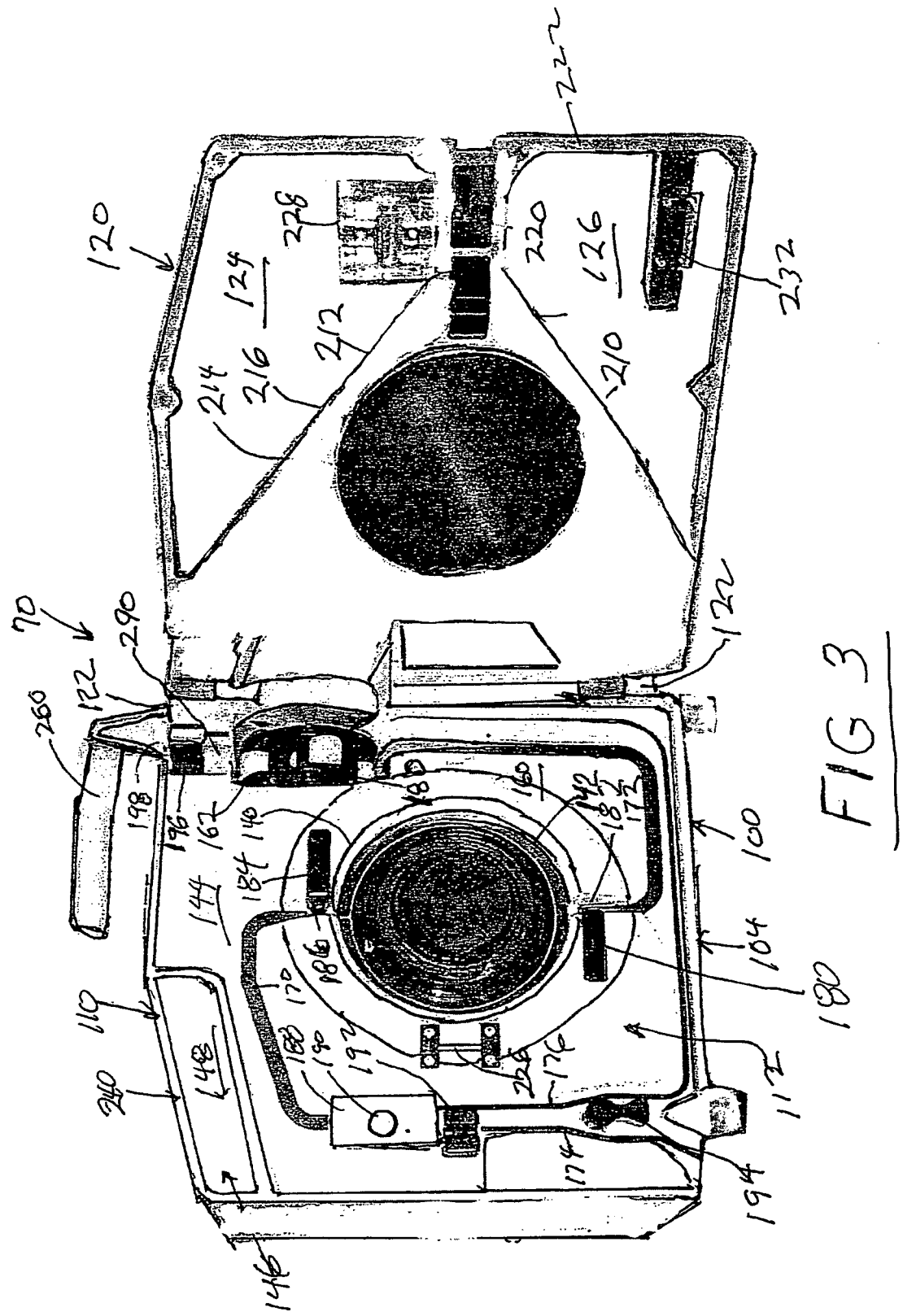
FIG. 3 is a is a front elevation view of the fluid processing device of FIG. 2 with its access door open to better show details of some of the mechanisms there-within.

Device 70 includes a housing 100 (FIGS. 2-5); which includes a top 102, a bottom 104, a left side 106, a right side 108 and a back 109 (FIG. 5) which together form a housing body 110 and define there within a component space 112 (FIG. 3). An access door 120, hingedly connected to body portion 110 as at 122 (FIGS. 3 & 4), permits access into component space 112 and to mechanisms and components housed and mounted within housing 100; as will be explained in greater detail herein after. Windows 124, 126, and 128, formed through access door 120, are covered with "Plexiglas", or similar transparent material, to facilitate observance of the processing taking place by device 70.

A conventionally available magnetic induction heater 140 (FIGS. 2 and 3), securely positioned within component space 112 of housing body 110, includes a heating ring 142 (FIG. 3) that projects through a component wall 144 (FIGS. 2 & 3) fixedly and vertically positioned within housing body 110. Suitable and conventional electric power is provided to therapeutic fluid processing device 70, through a power cord (not shown) that is to be connected to an electric outlet (not shown), and there from to heater 140. A substantially conventional computer 146 (FIG. 3), also fixedly positioned within housing body 110, along with its control and operating software and/or hardware 148, also receives power through the power cord (not shown). Device 70 may also be provided with back-up batteries (not shown) (rechargeable or otherwise) also housed within housing body 110 and suitably connected to the components and mechanisms there within that require electric power to operate. A conventional roller-type peristaltic pump 160, also positioned within housing body 110 and with a portion 162 of pump 160 extending out through wall 144, also receives suitable electric power through the power cord (not shown) and operates under control of computer 146 and its associated software/hardware 148 as will be explained in greater detail herein after.

Positioning grooves 170, 172 (FIG. 3) are formed in the surface of component wall 144, of housing 110, to receive specific sections of tubular fluid lines 60 (FIG. 2) of section 64 of disposable set 46. Positioning guidelines 174, 176 are also provided on wall 144 to facilitate positioning and placement of relatively narrower tubular fluid lines as will be further explained herein after. A temperature probe 180 (FIGS. 2 & 3) is mounted on wall 144 proximate a fluid entry 182 (FIG. 3) to heater 140 and another temperature probe 184 (FIGS. 2 & 3) is mounted on wall 144 at a fluid exit 186 (FIG. 3) from heater 140. Temperature probes 180, 184 are suitably connected to power and computer 146, and its software/hardware, and they are of the infrared type but other types of temperature probes may just as well be so mounted and used as will be further explained herein after. A substantially semi-cylindrical pressure chamber well 188, formed in wall 144, receives a pressure transducer 190, which is also mounted to wall 144 of housing 100 proximate an air detector 192. A diversion valve 194 is also mounted on wall 144 between fluid line positioning grooves 174, 176. A fluid out detector 196 is carried by wall 144 proximate a fluid entry 198 into device 70 and its fluid pump 160.

Access door 120 is formed with a door panel 210. An inner surface 212 (FIG. 3) of door panel mounts a ferrite, or iron core, magnetic plate 214 with a lip 216 extending out there from, for co-action with heater ring 142 of magnetic induction heater 140 and heat exchanger rings 218 (FIGS. 2 & 6) of disposable set 46; as will be hereinafter explained in greater detail. A door latch support 220 (FIGS. 3 & 4) extends from panel 210 to an edge 222 of access door 120 and supports a door latch 224 (FIG. 3) that co-operates with a door catch 226 that is carried by wall component 144. A pressure chamber support 228 (FIGS. 3 & 4) extends up from door latch support 220 for co-action with a pressure chamber 230 (FIG. 2) of disposable set 46 when pressure chamber 230 is positioned in pressure chamber well 188 (FIG. 3) proximate pressure transducer 190, as will be hereinafter explained in greater detail. A fluid tube holder 232 (FIGS. 3 & 4) extends inwardly (in the plane of the access door) from edge 222 of access door 120.

A computer monitor touch screen or display 240 (FIGS. 2-5, 7 & 8) is provided atop housing 100 to provide data output from computer 146 to the operator concerning operation of the therapeutic fluid processing device 70 and for the operator to provide instructions to computer 146, by way of touch screen 240 to control operation of device 70 and system 30. Device 70 is also provided with conventional phone-type input jacks 246 and 248 (FIG. 5) for connection, through conventional cables (not shown) to external temperature probes (not shown) if needed and at locations of the patient's body under physician instructions.

A carry handle 260 (FIGS. 2-5) is provided for device 70. Housing 100 of device 70 is further formed with an IV pole indent space 262 (FIGS. 2 & 5) having an IV pole entry space 264 of a size and configuration to receive IV pole 90. A device clamp 266 (FIG. 5) is movably mounted within body 110 of housing 100. Clamp 266 includes a clamp end 268 that is either: extendable from housing 100 into space 264 to co-act with IV pole 90 to clamp device 70 to IV pole 90 or retractable from space 264 to release device 70 from IV pole 90 and permit removal there-from. A device clamp-operating handle 270 is pivotally mounted at 272 for movement in a counter-clockwise direction from position "A" to position "B" to project clamp end 268 into space 264 for co-action with an IV pole 90 when device 70 is disposed to be secured to an IV pole 90. Pivoting of operating handle 270 from its position "B", clockwise about pivot 272, to position, "A" retracts clamp end 268 and releases device 70 from an IV Pole 90. A device support clamp 274, split at 276 and pivoted together at 278 to facilitate being secured to IV pole 90 to further support device 70 when secured onto IV pole 90, is provided with a set screw 280 to facilitate securing clamp 274 in place as will be further described herein-after. A protective washer 282, open at 284 is sized and configured to snap around IV pole 90, to further facilitate securing device 70 in place on IV pole 90. Support clamp 274 and protective washer 282 together provide a support assembly 286 to facilitate positioning device 70 on IV pole 90. An interlock block 290 (FIGS. 2 & 3) is also positioned in device 70. An on/off switch 292 (FIG. 2) is provided for device 70.

Figure 6:
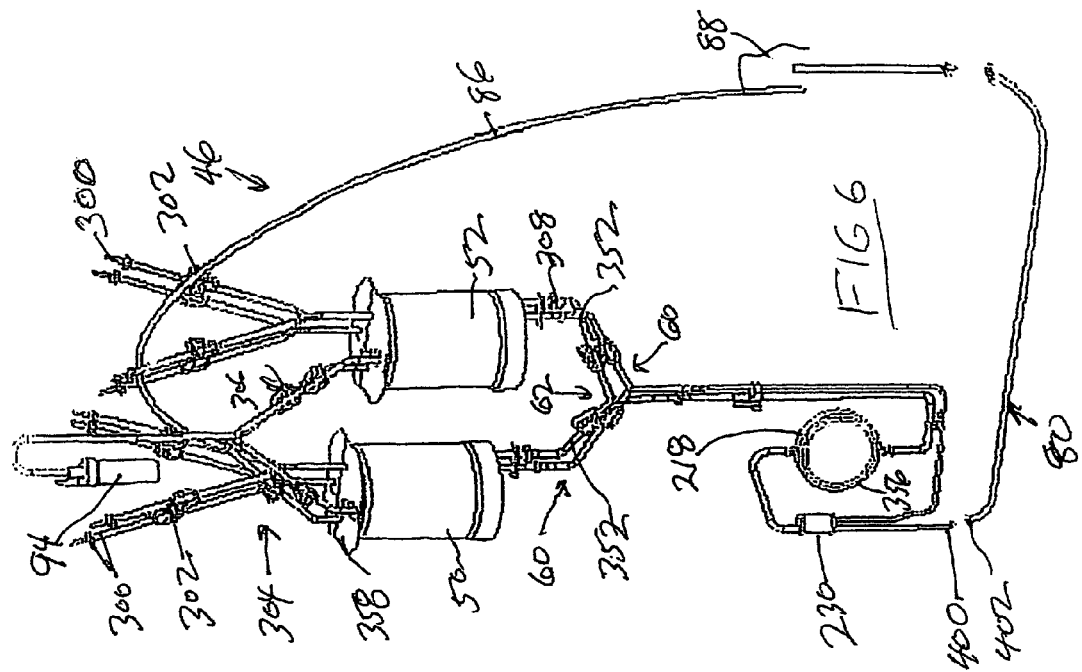
FIG. 6 is a perspective elevation view of the disposable set of FIG. 2, incorporating the instant invention.
Figure 7:
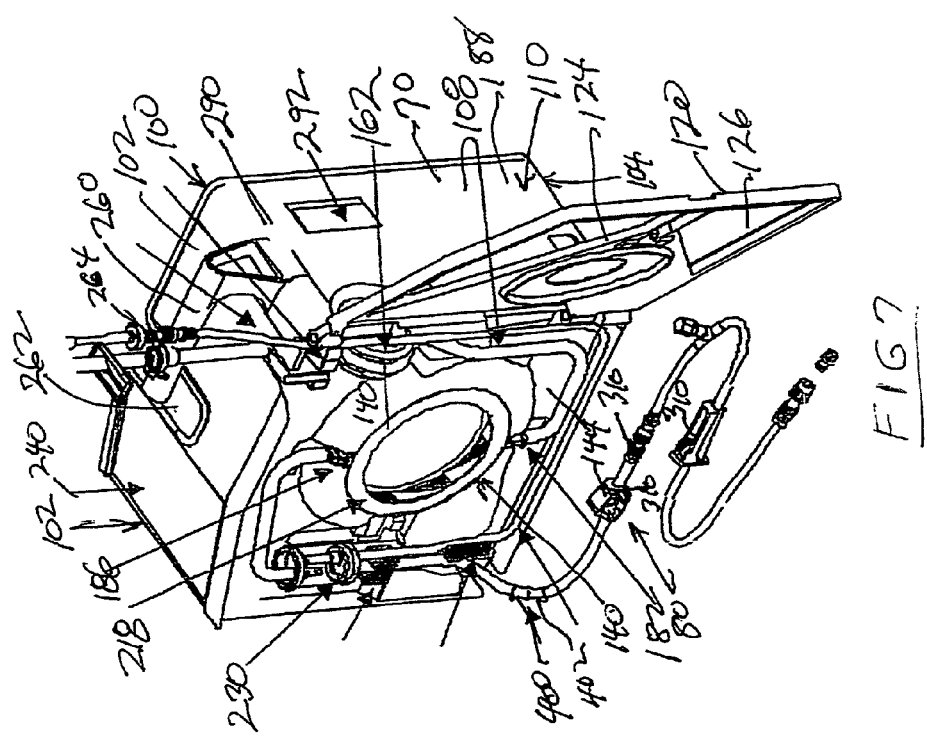
FIG. 7 is a perspective elevation view of the fluid showing a portion of the disposable set of FIGS. 2 and 6, installed within the fluid processing device of FIGS. 2-5, enlarged somewhat, to better show detail thereof.
Figures 8, 9:
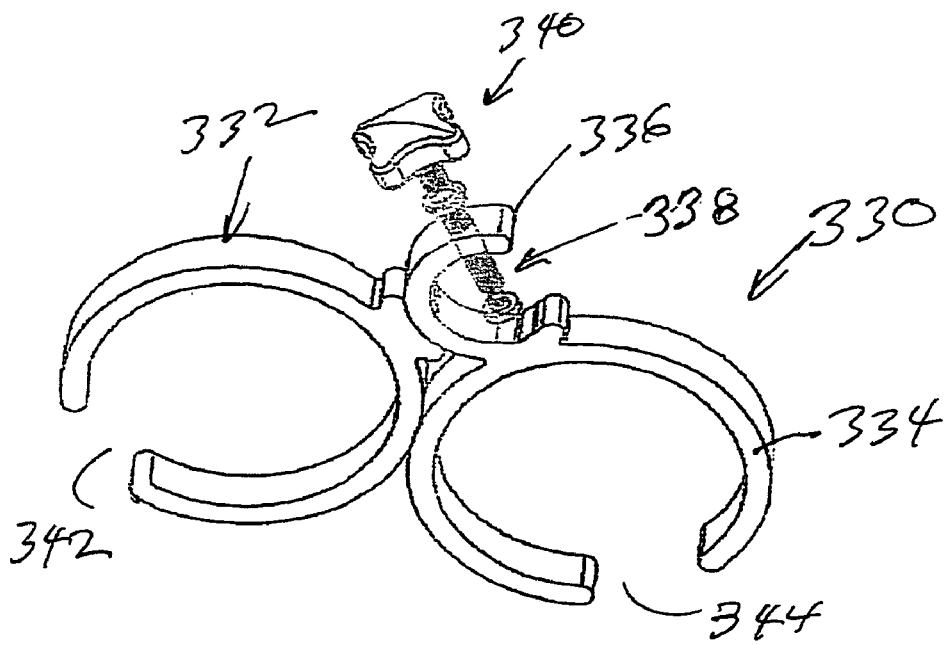
FIG. 8 is a face view of the control panel display/monitor for the fluid processing device of FIGS. 2-5.
FIG. 9 is a perspective view of a reservoir holding bracket for mounting the two fluid reservoirs of the disposable set of FIG. 6, to the IV pole, as shown in FIG. 2.

As set forth herein-above fluid disposable set 46 (FIGS. 2 and 6) includes a pair of reservoirs 50, 52 to be connected to IV bags 36, 38 (FIG. 2), when so required and when mounted on IV pole 90, to receive fluid there-from. The interconnections of reservoirs 50, 52 and IV bags 36, 38 (FIGS. 2 & 6) is accomplished through fluid lines 40 and "Y" connectors 42 as needed and in conventional manner. Conventional bag spikes 300 (FIG. 6) and bag clamps 302, as well as connectors 306 and quick connectors 308 may be utilized in setting up disposable set 46. For description purposes disposable set 46 has been divided into two sections with section 44 extending from fluid bags 36, 38 to reservoirs 50, 52 and set 64, with its fluid lines 60 and "Y" connectors 62 extending from reservoirs 50, 52 to and through fluid processing device 70. Check vales 309 and roller type clamps 310, as well as other clamps and connectors, similar to those of section 44 may be utilized, in conventional manner when setting up disposable set 46. Also included as part of disposable set 46 is a set of heat exchanger rings 320 and pressure chamber 230; as well as patient line to be divided, as needed, into fluid supply line 80 with its vent cap 322 (FIGS. 2 & 7) and fluid return line 86 (FIGS. 1 & 6). A dual reservoir holder 330 (FIGS. 2 & 8) includes reservoir receivers 332 and 334 that are sized and configured to receive, position and hold reservoirs 50, 52, respectively. A reservoir holder securing clamp 336 (FIG. 8), secured to both receivers 332 and 334, is formed with an opening 338 sized and configured to fit around IV pole 90, A thumb-type screw 340 is threaded through clamp 336 to facilitate securing holder 330 to IV pole 90. Receivers 332, 334 are formed with openings 342, 344 respectively that permit a sufficient degree of movement of holders 332, 334 to snugly receive and hold reservoirs 50 and 52. (FIGS. 2 and 6). While holder 320 has been shown with two receivers 332, 334 it may also be fabricated with a single reservoir receiver as well as being fabricated with reservoir receiver(s) of a size and configuration for the quantity of fluid to be held by the respective reservoir.

Figure 5:
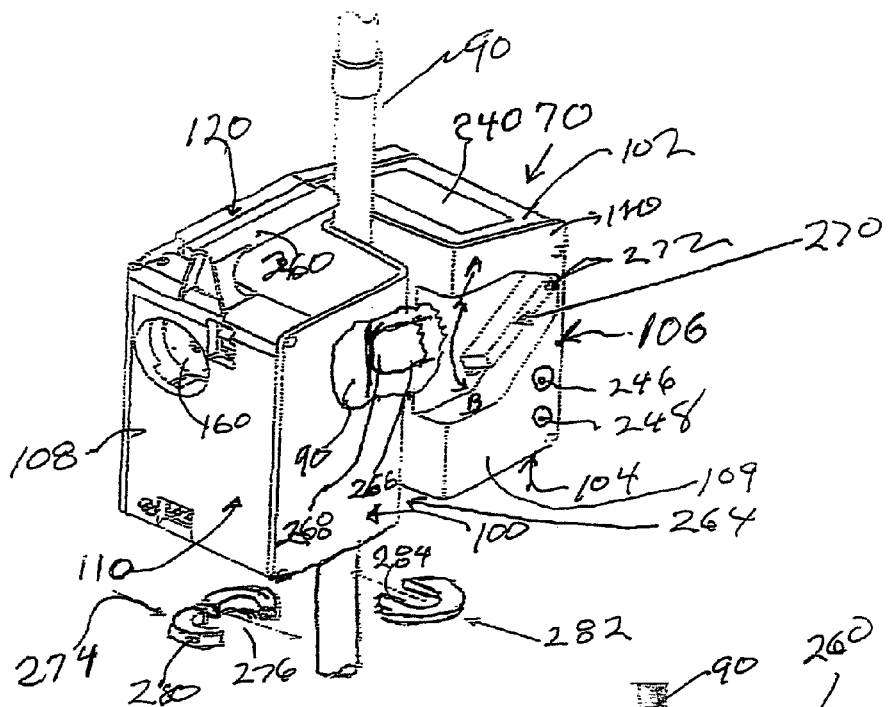
FIG. 5 is a perspective elevation view of the fluid processing device of FIGS. 2-4 showing same being mounted to the IV pole.

When a physician for a patient prescribes hyperthermia, 86 (FIG. 1) the patient 86 is usually placed in a proper atmosphere, such as a "sterile field" in an operating room. According to the instant hyperthermia system and procedure an IV pole 90 (FIG. 2), a therapeutic fluid processing device 70 and a disposable set 46 are made available. IV Pole 90, preferably, should be of the 5-wheel type with a maximum diameter 1¼". Support Assembly 286 (FIG. 5) is, preferably, secured approximately 30" above wheelbase 92 of IV pole 90 by installing support clamp 276, in its open position as shown in FIG. 5, around IV pole 90, closing support clamp 276 and tightening it in place using setscrew 280. Protective washer 282 is thereafter snapped in place on IV pole 90 above support clamp 276. With device clamp operating handle 270 rotated to its "A" position and device clamp end 268 retracted from space 264 device 70 is installed on pole 90 just above support assembly 286. Operating handle 270 is thereafter rotated, in the clockwise direction about its pivot 272, to project clamp end 268 against IV pole 90 to secure device 70 in place on IV pole 90. It is proper procedure to check that device 70 is secured in place and so that IV pole 90 will not tip over and that there is nothing obstructing air vents (not shown) provided bottom wall 104, or otherwise, of device 70. Reservoir holder 330 (FIGS. 2 & 8) is thereafter clamped onto IV pole 90 approximately 9" above processing device 70 (FIG. 2).

Reservoirs 50, 52 are removed from disposable set 46, using aseptic techniques, by, disconnecting luer connectors 358 (FIG. 6) and disconnecting fluid tubing 40 by pressing in the luer lock tab 360 and pulling out connector 358 and by disconnecting the thinner recirculation fluid line 40 by unscrewing its connector 358. Reservoirs 50, 52 when removed from disposable set 46 might best be placed on top of device 70 but other convenient dispositions might be selected by the user.

Figure 10:
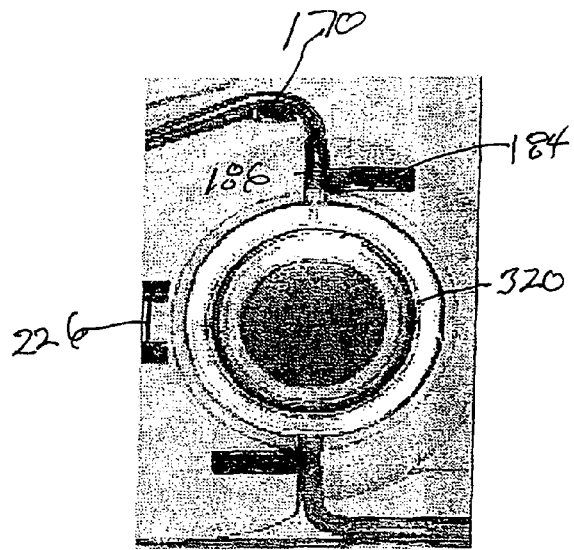
FIG. 10 is a partial elevation view inside the fluid processing device of FIGS. 2-5 and 7, showing the mounting there within of the heat exchanger of the disposable set of FIG. 6.
Figure 11:
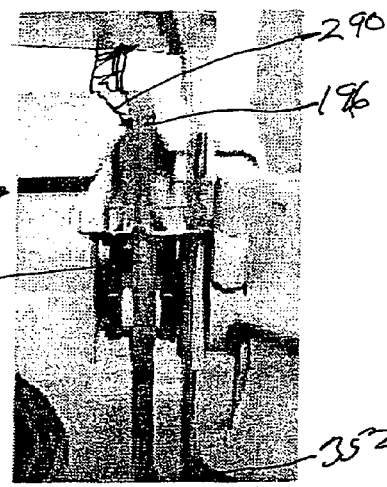
FIG. 11 is a partial elevation view inside the fluid processing device of FIGS. 2-5 and 7, showing the mounting there within of the interlock of the disposable set of FIG. 6 into the fluid out detector of the fluid processing device of FIGS. 2-5 and 7; and, FIG. 12 is a partial elevation view inside the fluid processing device of FIGS. 2-5 and 7, showing the mounting there within of the pressure chamber of the disposable set of FIG. 6 into a pressure chamber well of the fluid processing device of FIGS. 2-5 and 7.

With door 120 of device 70 (FIG. 3) open, heat exchanger rings 320 (FIGS. 6 & 10) of disposable set 46 are placed around heater rings 142 of heater 140. A red arrow (not shown) pointing up may be provided to facilitate installing rings 320 on heater 140 and Red tinted tubing may be utilized to correspond to a red stripe on device 70). Interlock block 290 (FIGS. 3 & 11) should be firmly positioned into fluid out detector 196. A section 350 (FIG. 11) of fluid line 60 (possibly blue tinted and curved to facilitate installation) is guided over the pump head of pump 160. Relatively thinner re-circulate fluid lines 352 (FIG. 6) extend down from the bottom of each reservoir 50 and 52 to be joined together by a "Y" connector 62 and to extend there from as single re-circulate line 352 that is placed in a grove to the right of pump 160. The fluid lines should not be kinked or twisted to facilitate proper fluid flow.

Figure 12:
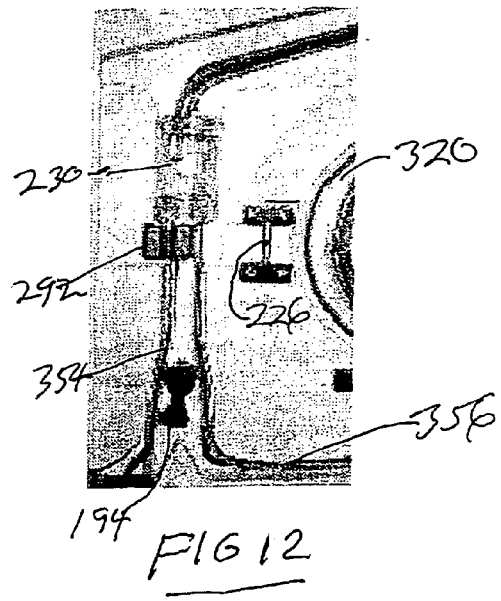

Pressure chamber 230 (FIGS. 2, 6 & 12) is placed into pressure chamber well 188 (FIG. 3) without applying excessive pressure or force thereto. A relative wide perfusion line 354 (FIG. 12), of disposable set 46, is then firmly inserted into air detector 192 (FIGS. 3 & 12) and to the left of diversion valve 194. A relatively thinner re-circulate fluid line 356 (FIG. 12), leading from pressure chamber 230, is position to the right of air detector 192 and to the right of diversion valve 194. Access door 120 (FIGS. 2 & 3) of device 70 should then be closed insuring that the fluid tubing is not caught thereby. Thereafter a section of fluid line, to be utilized for patient feed line 80 (FIGS. 1 & 2) and return line 86 is connected to the infuse line luer lock. The section of patient feed/return fluid line is preferably 16 feet in length but other lengths may be selected according to physician orders.

After reservoirs 50, 52 (FIG. 2) have been placed in reservoir receivers 332, 334 respectively they are to be assembled back into disposable set 46, using aseptic techniques. To the top of each of reservoirs 50, 52 there should be re-attached: two fluid supply tails 362; one vacuum relief valve 364; and a "Y" set for connecting a vacuum source 366 to an outer port 368 outside of a filter 370. To the bottom of each of reservoirs 50, 52 there should be attached: one "Y" set for reservoir outlet 372; one "Y" set for recirculation fluid line 374. Reservoir outlet 372, and recirculation line 374, should also be connected to a luer 376 of disposable set 46 and reservoir holder 330 should be adjusted to make sure that the two connection leads underneath reservoirs 50, 52 are not stretched or kinked.

To provide a hyperthermia fluid lavage to a portion of the body of patient 84 the system power cord (not shown) should be connected into a grounded, 3-prong, 20 Amp, AC receptacle. The external temperature interface cables (not shown) should be plugged into device 70 at input jacks 246, 248 (FIG. 5). Turn power on by firmly pressing on/off switch 292 (FIG. 2) to its "on" position. System 30, through its computer 146 and associated operating hardware/software 148, will perform a self-check to check the integrity of system parameters. A caution statement such as "For Hyperthermic Treatment Only. Not for infusion into the circulatory system" may appear on display 240. Press, "Agree" on display 240 and a "Password" screen may be displayed if a password is to be required. A factory default password, such as 111111 may be entered to set up system 30. Hang at least one 2-liter sterile fluid bag 36, 38 (FIG. 2) on the IV pole 90. However, as many fluid bags as ordered by a physician may be hug on IV pole 90. Preferably, fluid bags 36, 38 are to provide physician ordered therapeutic fluid(s) such as sterile normal saline, peritoneal dialysis solution, or other crystalloid solution. The bag spike cap should be removed from the IV bag(s) and the fluid bag(s) should be fully pierced to ensure that fluids flow freely. The ratchet clamp(s) for the respective pierced solution(s) should be opened. Display 240 may show a PRIME screen. Press PRIME to recirculate 100 ml of fluid at 500 ml/min to remove air and fill the system with fluid. A priming volume, 100 ml, countdown may displayed on display 240. Pump 160 is set to stop automatically when countdown reaches 0 ml. If priming has to be stopped, press STOP on display 240 and the prime volume countdown will remain on the screen. To resume priming system 30 Press RESUME PRIME on the display.

The section of patient line 88 to be utilized for the patient feed line 80 and return line 86, as referred to herein above, should be given to someone in the "sterile field", to be divided into patient feed line 80 and return line 86 (with "Y" connection), and then returned from the "sterile field". Also external temperature connections may be provided from the sterile field along with external temperature interface cables (not shown) to be there after connected to the device 70, white to white. Push firmly to assure full contact. Forced mating of the connectors can cause malfunction and interruption of electrical continuity. The external temperature probes (not shown), if needed, are placed at patient locations selected by the physician. Such probes may be Data scope 400 series disposable temperature probe with the white probe connector P/N 0206-03-0118-02 or otherwise and are connected to input jacks 246, 248 (FIG. 5) as described herein above. Return fluid line 86 (FIGS. 1 & 2) is connected to the luer lock of disposable set 46. A directional arrow may be imprinted on the patient line. One section of return line 86 is connected to a respective one of reservoirs 50, 52.

The patient in feed line 80 should be inspected to make certain that it is completely primed and free of air. This can be accomplished by pressing "PT. LINE PRIME" on display 240. System 30 will then prime at 400 ml/min. An inspection should be made to make sure that no air remains in patient line 80. When air is no longer visible, "STOP" on display 240 may be pressed. If there is, air bubbles after diversion valve 194, press "PT. LINE PRIME" on display 240 again to remove air. The prescribed solution(s) should be dropped into reservoir(s) 50, 52 either or both. As a caution, everyone involved may be informed that the prescribed solution(s) are ready to insure that only appropriate personnel are left in the room. "PERFUSE" on display 240, is then pressed and pump 160 starts pumping at 10 ml/min. The "750 ML/MIN" on display 240 should be pressed to operate pump 160 at 750 ml/min. The flow rate may be adjusted, as needed, by pressing "RATE●RATE" on display 240. The output temperature from heater 140 is adjusted from 37 degrees C. to 46 degrees C. by pressing "TARGET TEMP●/TARGET TEMP●" on display 240 to reach the specified output temperature. The set temperature is displayed in both "TARGET TEMP"* and "TARGET TEMP* on display 240. The actual fluid temperature, as it exits the heat exchanger rings 320, Tout, is also displayed on screen 240. Temperature is increased/decreased by 0.5 degrees C. every time key is pressed.

The prescribed solution(s) 32, 34 are pumped as directed by the surgeon. The vacuum is adjusted to facilitate fluid return. The speed of pump 160 should be regulated to keep the line pressure under the user-set pressure limit. Patient and system parameters should be checked regularly on screen 240 and system alarms should be responded to when and as needed. Additional sterile crystalloid or other solution IV bags 36, 38 should be spiked, as needed, per the surgeon. System 30 provides for a periodic beep when the pressure status line flashes and the periodic beep sounds while the system is under pressure control. Line pressure is mainly due to the small orifice of the catheters or any occlusions in the line. A pressure limit may be factory set to a maximum limit of 300 mmHg. Such pressure limit may however be changed as required. System 30 is also programmed to automatically purges air from the system after every two liters of fluid has been pumped. A "RATE" status line displays "REMOVING AIR" during this process. The volume readout (VOI) remains unchanged during automatic air purging and resumes counting when pumping resumes.

If there is fluid in the disposable set 46 when system 30 is not powered on, patient line 80 should be clamped closed when opening door 120 of device 70 to prevent uncontrolled fluid flow. If the flow rate is at or below 500 ml/min, the recirculation rate is temporarily set to 500 ml/min during automatic air purging. If the flow rate is above 500 ml/min, the recirculation rate is at the actual flow rate. When pumping resumes, the system returns to the previously set flow rate. If on/off switch 292 is not turned to STANDBY device, 70 will automatically switch to Battery Mode and will run until the battery is completely discharged and shut down.

When the procedure is over pump 160 should be stopped and the ratchet clamp(s) on reservoir outlets should be clamped closed. The vacuum should be increased, but not more than −150 mmHg, as needed, to facilitate emptying the body cavity of patient 84. If total volume exceeds 6 liters, an alternate source is required to empty the body cavity In order to turn device 70 back to ON, turn on/off switch 292 to STANDBY. Plug device 70*t* in the AC outlet and wait approximately 20 seconds before turning the power switch to ON. When all volume is reclaimed, clamp off patient line 80 and the bag spikes. Inflow, return line, and external disposable temperature probes (if used) are handed off the "sterile field" in orderly fashion and placed in a chemotherapy bucket along with disposable set(s) 46 and all bags and attachments. All should be disposed according to the hospital policy. On/off switch 292 should be moved to STANDBY.

In another embodiment of the instant invention reservoirs 50 and/or 52 continue to function, as herein above described, as mixing and containment vessels and as thermal reservoirs. Pressure chamber 230 (FIG. 6) still serves to provide fluid to patient fluid line 80 as well as to re-circulate line 352 which includes a "Y" connector 62 through which fluid is returned to the bottom of reservoirs 50 and 52 through separate sections of line 352 which each contain a check valve 308. Pressure chamber 230 has a number of functions, firstly operating as a bubble trap whose function is accomplished by gravitational separation of air from fluid when diversion valve 194 (FIGS. 3 & 12) is in an infuse position permitting fluid flow into patient infuse line 80. In that position of diversion valve 194 the recirculation line 352 is obstructed and patient line 80 is open. Fluid and any air present is forced into the chamber 230 (FIG. 6), by the peristaltic action of pump 160, through the top of chamber 230 and such fluid only exits from the bottom of pressure chamber 230 where fluid then continues to the infuse line 80 and to the patient 84. Fluid line 40, when threaded over the pump head delivers fluids downstream peristaltically when roller pump 160 is rotated. Heat exchanger rings 320 warm the fluid by converting energy generated by heater 140 by means of magnetic induction. Pressure chamber 230 secondly functions when diversion valve 194 (FIGS. 3 & 12) is in its re-circulate position (patient line 80 obstructed and re-circulate line 352 open), to return heated fluid to reservoirs 50 and or 52 and so that the peristaltic action of pump 160 will cause any air collected at the top of the bubble trap in pressure chamber 230 to also travel back to reservoirs 50, 52. Pressure chamber 230 thirdly functions, when a wall of pressure chamber 230 is in direct contact with pressure transducer 190 to provide feedback to computer 146 of the internal pressure within the fluid path.

This inventive embodiment also consists of the provision of a means to store heat energy within reservoirs 50 and/or 52 during off peak periods when there is relatively low fluid flow for use later when high fluid flow is required. To achieve this end input temperature probe 180 measures the temperature of the infusate fluid and, if need be, appropriate action is taken, as by turning diversion valve 194 to its re-circulate position. In that position the fluid is re-circulated from pressure chamber 230 through line 356 to and through reservoirs 50, 52, pump 160, heat exchange rings 320 and back to pressure chamber 230 to prewarm the fluid that is to be provided to patient 84. When temperature probe 180 indicates that the fluid is at a pre-selected temperature action of device 70 may be turned off and/or diversion valve 194 turned to its patient position. It is to be understood that this embodiment may be applied either to hyperthermia lavage procedures or to infusing other fluids by IV to patients' bloodstreams or for other medical procedures. It is to be also understood that the diversion valve 194 may be electronically operated under computer control.

In yet another embodiment of the instant invention the second reservoir may be used for the storage of packed red cells outside of the recirculation path for the purpose of minimizing the number of passes through peristaltic pump 160. In still a further embodiment of the instant invention, an occlusive roller pump (not shown) whose operation is to act as a metering device replaces diversion valve 194. A patient fluid feed line is placed within this pump and a re-circulation line is allowed to flow freely. The main infusion would operate at a higher flow rate and the roller pump located at the diversion valve would meter flow to the patient. The algebraic difference between the two pumps would be returned, heated, to the reservoir.

as various changes could be made in the above constructions without departing from the scope of the invention, it should be understood that all matter contained in the above description and/or shown in the accompanied drawing should be interpreted as illustrative and not in a limited sense.

What is claimed is:

1. A hyperthermia system for providing fluid for a body comprising;
   (a) a fluid processing device including a fluid heater and a fluid pump;
   (b) fluid flow tubing providing a fluid flow path to and through said fluid processing device for subsequent flow to the body and from the body back to said fluid processing device;
   (c) said fluid pump to provide a predetermined fluid flow rate that is not too excessive to the body;
   (d) said fluid heater comprising an electro magnetic inductive fluid heating device to heat the fluid to a temperature not to exceed a temperature which is just a few degrees centigrade above normothermic for the body.

2. The hyperthermia system of claim 1; wherein said predetermined fluid flow rate is not to exceed 750 ml/min.

3. The hyperthermia system of claim 1; wherein said fluid pump is a roller-type peristaltic volumetric pump.

4. The hyperthermia system of claim 1: wherein said fluid processing device is of a size and weight that permits it to be mounted on a conventionally available standard IV pole.

5. The hyperthermia system of claim 1; wherein said fluid processing device further includes:
   (a) a first ultrasonic air detector proximate an inlet for fluid to said fluid flow processing device and a second ultrasonic air detector proximate an outlet for fluid from said fluid processing device to substantially eliminate air from the fluid;
   (b) pressure control mechanism to facilitate pressure control for the fluid passing through said fluid processing device; and
   (c) touch screen type computer control co-acting with said first and second air detectors and said pressure control mechanism as well as with temperature sensors, for sensing fluid temperature just before the fluid is subjected to heat from said fluid heater and just after the fluid has been heated by said fluid heater, for continuous real time temperature monitoring and to otherwise facilitate fluid processing through said fluid processing device.

6. The hyperthermia system of claim 1; wherein the fluid to be processed may be human blood, crystalloid or a therapeutic fluid such as chemotherapy solution.

7. The hyperthermia system of claim 1; wherein said fluid flow tubing is included as part of a single use disposable set which also includes a heat exchanger configured and positioned to co-act with said electro magnetic inductive fluid heating device to heat fluid during the flow of fluid through said fluid processing device.

8. A hyperthermia system for providing fluid for a body: comprising;
   (a) a fluid processing device including a fluid heater and a fluid pump;
   (b) fluid flow tubing providing a first fluid flow path to and through said fluid processing device for subsequent flow to the body and from the body back to said fluid processing device;
   (c) said fluid pump to provide a predetermined fluid flow rate;
   (d) said fluid heater heating the fluid to a predetermined temperature;
   (e) said fluid flow tubing providing a second fluid flow path back to and through said fluid processing device; and
   (f) a fluid path diversion control for directing the fluid into either said first path or said second path (g) said fluid heater comprising an electro magnetic inductive fluid heating device to heat the fluid to a temperature not to exceed a temperature which is just a few degrees centigrade above normothermic for the body.

9. A hyperthermia system for providing fluid for a body: comprising;
   (a) fluid processing means for processing a predetermine fluid, including fluid heating means to heat the fluid and a fluid pump means to pump the fluid through fluid passage means;
   (b) fluid flow tubing means providing first fluid passage means to and through said fluid processing means for subsequent flow to the body and from the body back to said fluid processing means;
   (c) said fluid pump means providing a predetermined fluid flow rate;
   (d) said fluid heater heating means heating the fluid to a predetermined temperature;
   (e) said fluid flow tubing means providing second fluid flow passage means back to and through said fluid processing means; and
   (f) fluid path diversion control means for directing the fluid into either said first passage means or said second passage means (g) said fluid heater comprising an electro magnetic inductive fluid heating device to heat the fluid to a temperature not to exceed a temperature which is just a few degrees centigrade above normothermic for the body.

10. The process of claim 9 including selecting said second fluid path during slack time.

11. A hyperthermia system for providing fluid for a body: comprising;
    (a) fluid processing means for processing a fluid, including
       (1) electro magnetic inductive fluid heating means for heating the fluid;
       (2) fluid passage means for directing the fluid when being pumped to and through said fluid processing means for subsequent flow to a body and from the body back to said fluid processing means; and
       (2) fluid pump means for pumping the fluid through said fluid passage means;
    (b) fluid flow tubing means for providing said fluid passage means
    (c) said fluid pump means providing a predetermined fluid flow rate;
    (d) said fluid heater heating means heating the fluid to a predetermined temperature; and
    (e) said predetermined temperature not to exceed a physiological temperature which is just a few degrees above normative for the body.

12. The hyperthermia system of claim 11; wherein said disposable set means also includes heat exchanger means configured and positioned to co-act with said fluid heater means to heat the fluid during the flow of the fluid through the fluid processing means.

* * * * *